(12) United States Patent
Silverman et al.

(10) Patent No.: US 9,249,149 B2
(45) Date of Patent: *Feb. 2, 2016

(54) DEUTERATED DERIVATIVES OF RUXOLITINIB

(71) Applicant: Concert Pharmaceuticals, Inc., Lexington, MA (US)

(72) Inventors: I. Robert Silverman, Arlington, MA (US); Julie F. Liu, Lexington, MA (US); Adam J. Morgan, Ashland, MA (US); Bhaumik Pandya, Arlington, MA (US); Scott L. Harbeson, Cambridge, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/707,912

(22) Filed: May 8, 2015

(65) Prior Publication Data

US 2015/0239896 A1 Aug. 27, 2015

Related U.S. Application Data

(63) Continuation of application No. 14/570,954, filed on Dec. 15, 2014, which is a continuation-in-part of application No. PCT/US2013/045919, filed on Jun. 14, 2013.

(60) Provisional application No. 61/660,428, filed on Jun. 15, 2012, provisional application No. 61/678,795, filed on Aug. 2, 2012, provisional application No. 61/917,589, filed on Dec. 18, 2013.

(51) Int. Cl.
| | |
|---|---|
| *C07D 487/04* | (2006.01) |
| *A61K 31/519* | (2006.01) |
| *A61K 45/06* | (2006.01) |
| *A61P 35/00* | (2006.01) |

(52) U.S. Cl.
CPC ............ *C07D 487/04* (2013.01); *A61K 31/519* (2013.01); *A61K 45/06* (2013.01); *C07B 2200/05* (2013.01)

(58) Field of Classification Search
CPC ............................. C07D 487/04; A61K 31/519
See application file for complete search history.

(56) References Cited

U.S. PATENT DOCUMENTS

| | | | |
|---|---|---|---|
| 6,221,335 B1* | 4/2001 | Foster ........................... | 424/1.81 |
| 6,440,710 B1* | 8/2002 | Keinan et al. ................. | 435/148 |
| 6,603,008 B1* | 8/2003 | Ando et al. ................. | 546/269.7 |
| 7,517,990 B2* | 4/2009 | Ito et al. ........................ | 546/184 |
| 7,598,257 B2 | 10/2009 | Rodgers et al. | |
| 2007/0082929 A1* | 4/2007 | Gant et al. ..................... | 514/338 |
| 2007/0135461 A1 | 6/2007 | Rodgers et al. | |
| 2007/0197695 A1* | 8/2007 | Potyen et al. .................. | 524/110 |
| 2008/0103122 A1* | 5/2008 | Veltri ........................ | 514/210.02 |
| 2008/0312258 A1 | 12/2008 | Rodgers et al. | |

FOREIGN PATENT DOCUMENTS

| | | |
|---|---|---|
| WO | WO 95/26325 A2 | 10/1995 |
| WO | WO 2007/118651 A1 | 10/2007 |
| WO | WO 2013/188783 A1 | 12/2013 |

OTHER PUBLICATIONS

Dyck, Journal of Neurochemistry vol. 46 Issue 2, pp. 399-404 (1986).*
Tonn, Biological Mass Spectrometry vol. 22 Issue 11, pp. 633-642 (1993).*
Haskins, Biomedical Spectrometry vol. 9 Issue 7, pp. 269-277 (1982.*
Wolen, Journal of Clinical Pharmacology 1986; 26: 419-424.*
Browne, Journal of Clinical Pharmacology1998; 38: 213-220.*
Baillie, Pharmacology Rev.1981; 33: 81-132.*
Gouyette, Biomedical and Environmental Mass Spectrometry, vol. 15, 243-247 (1988).*
Cherrah, Biomedical and Environmental Mass Spectrometry vol. 14 Issue 11, pp. 653-657 (1987).*
Pieniaszek, J Clin Pharmacol.1999; 39: 817-825.*
Honma et al., Drug Metab Dispos 15 (4): 551 (1987).*
Baille, T. A., "The Use of Stable Isotopes in Pharmacological Research," *Pharmacological Reviews*, 33(2): 81-132 (1981).
Browne, T. R., "Stable Isotope Techniques in Early Drug Development: An Economic Evaluation," *J. Clin. Pharmacol.*, 38: 213-220 (1998).
Buteau, "Deuterated Drugs: Unexpectedly Nonobvious?," *Journal of High Technology Law, Suffolk University Law School*, X1:22-74 (2009).

(Continued)

*Primary Examiner* — Susanna Moore
(74) *Attorney, Agent, or Firm* — Foley Hoag LLP

(57) ABSTRACT

The present invention in one embodiment provides a compound of Formula A:

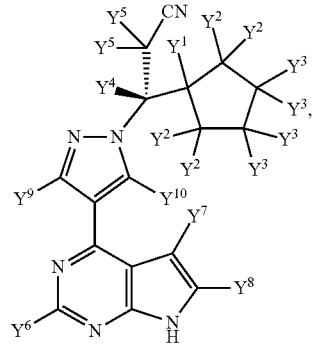

Formula A or a pharmaceutically acceptable salt thereof; pharmaceutical compositions comprising the compound; and methods of treating the indications disclosed herein.

15 Claims, 1 Drawing Sheet

(56) References Cited

OTHER PUBLICATIONS

Cherrah, Y., et al., "Study of Deuterium Isotope Effects on Protein Binding by Gas Chromatography/Mass Spectrometry. Caffeine and Deuterated Isotopomers," *Biomedical and Environmental Mass Spectrometry*, 14: 653-657 (1987).

Dyck, L. E., et al., "Effects of Deuterium Substitution on the Catabolism of β-Phenylethylamine: An In Vivo Study," *Journal of Neurochemistry*, 46(2): 399-404 (1986).

Fisher, M.B. et al., "The Complexities Inherent in Attempts to Decrease Drug Clearance by Blocking Sites of CYP-Mediated Metabolism," Curr. Opin. Drug Discov. Devel., 9(1):101-109 (2006).

Foster, A. B., "Deuterium Isotope Effects in Studies of Drug Metabolism," *Trends in Pharmacological Sciences*, 5: 524-527 (1984).

Foster, A. B., "Deuterium Isotope Effects in the Metabolism of Drugs and Xenobiotics: Implications for Drug Design," *Advances in Drug Research*, 14: 1-40 (1985).

Gouyette, A., "Synthesis of Deuterium-labelled Elliptinium and its Use in Metabolic Studies," *Biomedical and Environmental Mass Spectrometry*, 15: 243-247 (1988).

Haskins, N. J., "The Application of Stable Isotopes in Biomedical Research," Biomedical Mass Spectrometry, 9(7): 269-277 (1982).

Honma S., et al., "The Metabolism of Roxatidine Acetate Hydrochloride," Drug Metabolism and Disposition, 15(4): 551-559 (1987).

Kushner, D.J. et al., "Pharmacological Uses and Perspectives of Heavy Water and Deuterated Compounds," Can. J. Physiol. Pharmacol., 77:79-88 (1999).

Ostojic, et al., "Ruxolitinib: a new JAK1/2 Inhibitor that Offers Promising Options for Treatment of Myelofibrosis,"*Future Oncology*, 7(9): 1035-1043 (2011).

Pieniaszek, H. J., et al., "Moricizine Bioavailability via Simultaneous, Dual, Stable Isotope Administration: Bioequivalence Implications," J. Clin. Pharmacol, 39: 817-825 (1999).

Notification Concerning Transmittal of International Preliminary Report on Patentability, International Application No. PCT/US2013/045919, entitled: "Deuterated Derivatives of Ruxolitinib," Date of Mailing: Dec. 16, 2014.

Notification of the Transmittal of the International Search Report and the Written Opinion of the International Searching Authority, International Application No. PCT/US2013/045919, entitled: "Deuterated Derivatives of Ruxolitinib," Date of Mailing: Jul. 31, 2013.

Shilling, et al., "Metabolism, Excretion, and Pharmacokinetics of [$^{14}$C]INCBO18424, A Selective Janus Tyrosine Kinase ½ Inhibitor, in Humans," *Drug Metabolism and Disposition*, 38(11):2023-2031 (2010).

Tonn G. R., et al., "Simultaneous Analysis of Diphenhydramine and a Stable Isotope Analog ($^2$H$_{10}$) Diphenhydramine Using Capillary Gas Chromatography with Mass Selective Detection in Biological Fluids from Chronically Instrumented Pregnant Ewes," Biological Mass Spectrometry, 22: 633-642 (1993).

Wolen, R. L., "The Application of Stable Isotopes to Studies of Drug Bioavailability and Bioequivalence," J. Clin. Pharmacol., 26: 419-424 (1986).

FDA Prescribing Information for JAKAFI™, Revised Nov. 2011, pp. 1-23.

Alsachim Online Catalog, "Drugs and Metabolitics—May 2012" [online], [Retrieved on Nov. 8, 2013]. Retrieved from the internet: http://www.alsachim.com/catalog.extract-drugs.metabolities-May.2012, 2 pgs.

Alsachim Online Product, "Ruxolitinib-D9 (CAS: 941678-49-5 Unlabeled)—Drugs and Metabolites" [online], online publication date unknown [Retrieved on Sep. 3, 2013]. Retrieved from the internet: http://www.alsachim.com/product-C3600-drugs.metabolites-Ruxolitinib-D9.html, 1 pg.

Unpublished Pending U.S. Appl. No. 14/570,954, Titled: "Deuterated Derivatives of Roxolitinib," by Inventor Silverman et al., filed Dec. 15, 2014.

Fukuto et al., "Determination of the Mechanism of Demethylenation of (Methylenedioxy)phenyl Compounds by Cytochrome P450 Using Deuterium Isotope Effects," J. Med. Chem. 34: 2871-2876, 1991.

\* cited by examiner

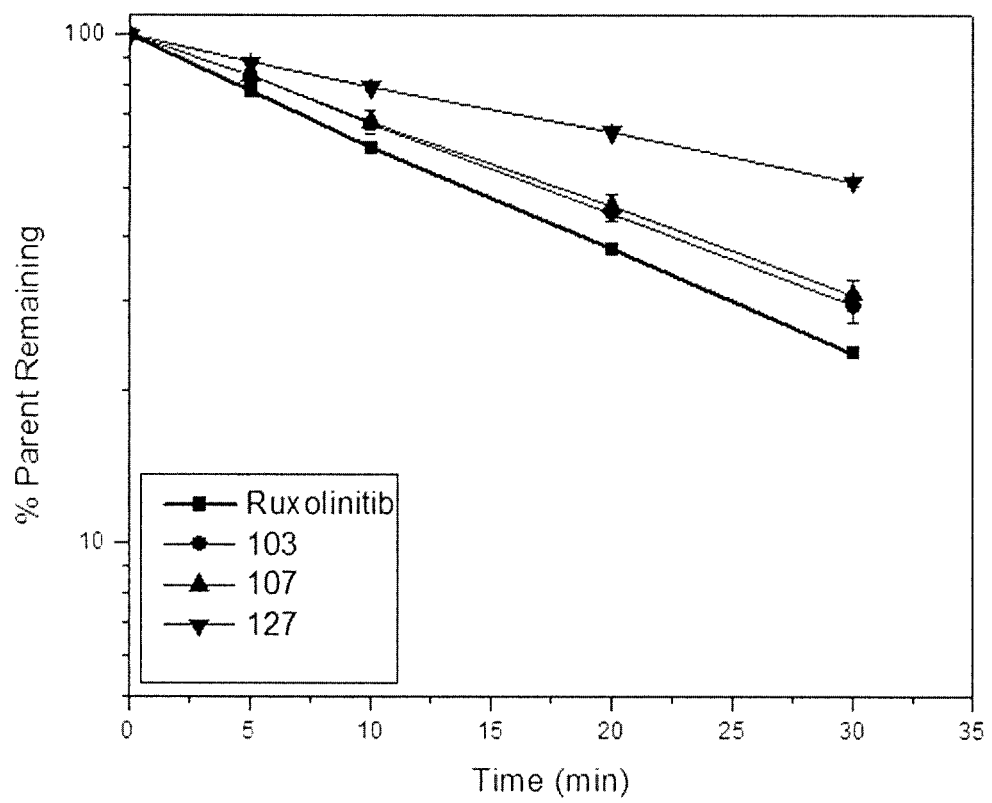

DEUTERATED DERIVATIVES OF RUXOLITINIB

RELATED APPLICATIONS

This application is a continuation of U.S. application Ser. No. 14/570,954, filed Dec. 15, 2014, which is a continuation-in-part of International Application No. PCT/US2013/045919, which designated the United States and was filed on Jun. 14, 2013, published in English, which claims the benefit of U.S. Provisional Application No. 61/660,428, filed Jun. 15, 2012, and U.S. Provisional Application No. 61/678,795, filed Aug. 2, 2012. U.S. application Ser. No. 14/570,954 also claims the benefit of U.S. Provisional Application No. 61/917,589, filed Dec. 18, 2013. The entire teachings of the above applications are incorporated herein by reference.

BACKGROUND OF THE INVENTION

Many current medicines suffer from poor absorption, distribution, metabolism and/or excretion (ADME) properties that prevent their wider use or limit their use in certain indications. Poor ADME properties are also a major reason for the failure of drug candidates in clinical trials. While formulation technologies and prodrug strategies can be employed in some cases to improve certain ADME properties, these approaches often fail to address the underlying ADME problems that exist for many drugs and drug candidates. One such problem is rapid metabolism that causes a number of drugs, which otherwise would be highly effective in treating a disease, to be cleared too rapidly from the body. A possible solution to rapid drug clearance is frequent or high dosing to attain a sufficiently high plasma level of drug. This, however, introduces a number of potential treatment problems such as poor patient compliance with the dosing regimen, side effects that become more acute with higher doses, and increased cost of treatment. A rapidly metabolized drug may also expose patients to undesirable toxic or reactive metabolites.

Another ADME limitation that affects many medicines is the formation of toxic or biologically reactive metabolites. As a result, some patients receiving the drug may experience toxicities, or the safe dosing of such drugs may be limited such that patients receive a suboptimal amount of the active agent. In certain cases, modifying dosing intervals or formulation approaches can help to reduce clinical adverse effects, but often the formation of such undesirable metabolites is intrinsic to the metabolism of the compound.

In some select cases, a metabolic inhibitor will be co-administered with a drug that is cleared too rapidly. Such is the case with the protease inhibitor class of drugs that are used to treat HIV infection. The FDA recommends that these drugs be co-dosed with ritonavir, an inhibitor of cytochrome P450 enzyme 3A4 (CYP3A4), the enzyme typically responsible for their metabolism (see Kempf, D. J. et al., Antimicrobial agents and chemotherapy, 1997, 41(3): 654-60). Ritonavir, however, causes adverse effects and adds to the pill burden for HIV patients who must already take a combination of different drugs. Similarly, the CYP2D6 inhibitor quinidine has been added to dextromethorphan for the purpose of reducing rapid CYP2D6 metabolism of dextromethorphan in a treatment of pseudobulbar affect. Quinidine, however, has unwanted side effects that greatly limit its use in potential combination therapy (see Wang, L et al., Clinical Pharmacology and Therapeutics, 1994, 56(6 Pt 1): 659-67; and FDA label for quinidine at www.accessdata.fda.gov).

In general, combining drugs with cytochrome P450 inhibitors is not a satisfactory strategy for decreasing drug clearance. The inhibition of a CYP enzyme's activity can affect the metabolism and clearance of other drugs metabolized by that same enzyme. CYP inhibition can cause other drugs to accumulate in the body to toxic levels.

A potentially attractive strategy for improving a drug's metabolic properties is deuterium modification. In this approach, one attempts to slow the CYP-mediated metabolism of a drug or to reduce the formation of undesirable metabolites by replacing one or more hydrogen atoms with deuterium atoms. Deuterium is a safe, stable, non-radioactive isotope of hydrogen. Compared to hydrogen, deuterium forms stronger bonds with carbon. In select cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M I et al, J Pharm Sci, 1975, 64:367-91; Foster, A B, Adv Drug Res 1985, 14:1-40 ("Foster"); Kushner, D J et al, Can J Physiol Pharmacol 1999, 79-88; Fisher, M B et al, Curr Opin Drug Discov Devel, 2006, 9:101-09 ("Fisher")). Many of the examples in these references report a local deuterium isotope effect (an effect on the rate of metabolism at a specific site of deuteration in the substrate) rather than the effect of deuteration on the overall metabolic stability of the drug, i.e., the overall substrate consumption via metabolism. The reported results of those studies measuring deuterium substitution's effect on overall metabolic stability are variable and unpredictable. For some compounds deuteration caused decreased metabolic clearance in vivo. For others, there was no change in metabolism. Still others demonstrated increased metabolic clearance. The variability in deuterium effects has also led experts to question or dismiss deuterium modification as a viable drug design strategy for inhibiting adverse metabolism (see Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem. 1991, 34, 2871-76). Many drugs have multiple sites where metabolism is possible. The site(s) where deuterium substitution is required and the extent of deuteration necessary to see an effect on metabolism, if any, will be different for each drug.

Ruxolitinib phosphate, is a heteroaryl-substituted pyrrolo[2,3-d]pyrimidines also known as 3(R)-cyclopentyl-3-[4-(7H-pyrrolo[2,3-d]pyrimidin-4-yl)-1H-pyrazol-1-yl]propanenitrile phosphate and as (R)-3-(4-(7H-pyrrolo[2,3-d]pyrimidin-4-yl)-1H-pyrazol-1-yl)-3-cyclopentylpropanenitrile phosphate, inhibits Janus Associated Kinases (JAKs) JAK1 and JAK2. These kinases mediate the signaling of a number of cytokines and growth factors important for hematopoiesis and immune function. JAK signaling involves recruitment of STATs (signal transducers and activators of transcription) to cytokine receptors, activation and subsequent localization of STATs to the nucleus leading to modulation of gene expression.

Ruxolitinib phosphate is currently approved for the treatment of patients with intermediate or high-risk myelofibrosis, including primary myelofibrosis, post-polycythemia vera myelofibrosis and post-essential thrombocythemia myelofibrosis. Ruxolitinib phosphate is also currently in clinical trials for the treatment of essential thrombocythemia, pancreatic cancer, prostate cancer, breast cancer, leukemia, non-Hodgkin's lymphoma, multiple myeloma and psoriasis.

Three metabolites in humans have been identified as active, that resulting from hydroxylation at the 2-position on the cyclopentyl moiety, that resulting from hydroxylation at the 3-position on the cyclopentyl moiety and the ketone resulting from further oxidation at the 3-position on the cyclopentyl moiety. (See Shilling, A. D. et al., Drug Metabolism and Disposition, 2010, 38(11): 2023-2031; FDA Prescribing Information and US20080312258).

The most common hematologic adverse reactions associated with the dosing of ruxolitinib are thrombocytopenia and anemia. The most common non-hematologic adverse reactions are bruising, dizziness and headache.

Despite the beneficial activities of ruxolitinib, there is a continuing need for new compounds to treat the aforementioned diseases and conditions.

SUMMARY OF THE INVENTION

This invention relates to novel heteroaryl-substituted pyrrolo[2,3-d]pyrimidines, and pharmaceutically acceptable salts thereof. This invention also provides compositions comprising a compound of this invention and the use of such compositions in methods of treating diseases and conditions that are beneficially treated by administering an inhibitor of Janus-associated kinase with selectivity for subtypes 1 and 2 (JAK1/JAK2).

BRIEF DESCRIPTION OF THE DRAWINGS

The figure shows the results of metabolic stability testing of the referenced compounds.

DETAILED DESCRIPTION OF THE INVENTION

Definitions

The term "treat" means decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of ruxolitinib will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3000 times greater than the natural abundance of deuterium, which is 0.015% (i.e., at least 45% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species in which the chemical structure differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The invention also provides salts of the compounds of the invention.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-l-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The compounds of the present invention (e.g., compounds of Formula I or Formula A), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "mammal" as used herein includes a human or a non-human animal, such as mouse, rat, guinea pig, dog, cat, horse, cow, pig, monkey, chimpanzee, baboon, or rhesus. In one embodiment, the mammal is a non-human animal. In another embodiment, the mammal is a human.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "Stereoisomer" refers to both enantiomers and diastereomers. "Tert" and "t-" each refer to tertiary. "US" refers to the United States of America.

"Substituted with deuterium" refers to the replacement of one or more hydrogen atoms with a corresponding number of deuterium atoms.

Throughout this specification, a variable may be referred to generally (e.g.,"each R") or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

The present invention in one embodiment provides a compound of Formula A:

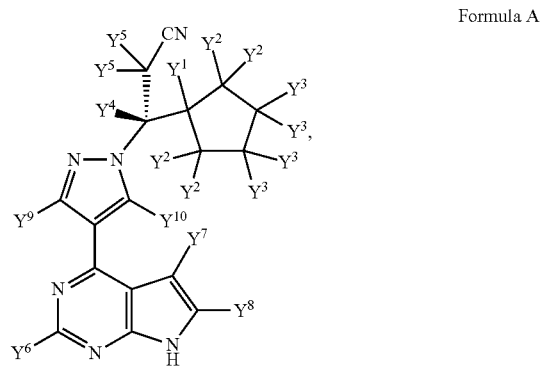

Formula A or a pharmaceutically acceptable salt thereof, wherein:

$Y^1$ is selected from hydrogen and deuterium;

each $Y^2$ is independently selected from hydrogen and deuterium, provided that each $Y^2$ attached to a common carbon is the same;

each $Y^3$ is independently selected from hydrogen and deuterium, provided that each $Y^3$ attached to a common carbon is the same;

$Y^4$ is selected from hydrogen and deuterium;

each $Y^5$ is the same and is selected from hydrogen and deuterium; and $Y^6$, $Y^7$, $Y^8$, $Y^9$, and $Y^{10}$ are each independently selected from hydrogen and deuterium; provided that when $Y^1$ is hydrogen, each $Y^2$ and each $Y^3$ are hydrogen, $Y^4$ is hydrogen, and each of $Y^6$, $Y^7$, $Y^8$, $Y^9$, and $Y^{10}$ is hydrogen, then each $Y^5$ is deuterium.

In one embodiment of Formula A each $Y^2$ is the same, each $Y^3$ is the same and each $Y^5$ is the same. In one aspect of this embodiment, each $Y^2$ is deuterium. In a further aspect each $Y^3$ is deuterium. In another further aspect each $Y^3$ is hydrogen. In another aspect of this embodiment, each $Y^2$ is hydrogen. In a further aspect each $Y^3$ is deuterium. In another further aspect each $Y^3$ is hydrogen. In one example of any of the foregoing aspects, $Y^1$ is deuterium. In another example of any of the foregoing aspects, $Y^1$ is hydrogen. In a more particular example of any of the foregoing aspects, $Y^1$ is deuterium, $Y^4$ is deuterium, and each $Y^5$ is deuterium. In another more particular example of any of the foregoing aspects, $Y^1$ is deuterium, $Y^4$ is deuterium, and each $Y^5$ is hydrogen. In another more particular example of any of the foregoing aspects, $Y^1$ is deuterium, $Y^4$ is hydrogen, and each $Y^5$ is hydrogen. In another more particular example of any of the foregoing aspects, $Y^1$ is hydrogen, $Y^4$ is hydrogen, and each $Y^5$ is hydrogen. In another more particular example of the foregoing aspects, $Y^1$ is hydrogen, $Y^4$ is hydrogen, and each $Y^5$ is deuterium. In another more particular example of any of the foregoing aspects, $Y^1$ is hydrogen, $Y^4$ is deuterium, and each $Y^5$ is deuterium. In another more particular example of any of the foregoing aspects, $Y^1$ is hydrogen, $Y^4$ is deuterium, and each $Y^5$ is hydrogen.

In one embodiment, Y⁶ is deuterium. In one aspect of this embodiment, each of Y⁷ and Y⁸ is deuterium. In another aspect of this embodiment, each of Y⁷ and Y⁸ is hydrogen.

In one embodiment, Y⁶ is hydrogen. In one aspect of this embodiment, each of Y⁷ and Y⁸ is deuterium. In another aspect of this embodiment, each of Y⁷ and Y⁸ is hydrogen.

The present invention in one embodiment provides a compound of Formula I:

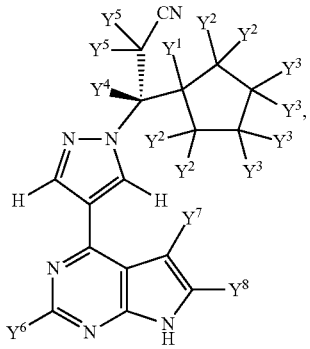

Formula I or a pharmaceutically acceptable salt thereof, wherein:
Y¹ is selected from hydrogen and deuterium;
each Y² is independently selected from hydrogen and deuterium, provided that each Y² attached to a common carbon is the same;
each Y³ is independently selected from hydrogen and deuterium, provided that each Y³ attached to a common carbon is the same;
Y⁴ is selected from hydrogen and deuterium;
each Y⁵ is the same and is selected from hydrogen and deuterium; and
Y⁶, Y⁷, and Y⁸ are each independently selected from hydrogen and deuterium; provided that when Y¹ is hydrogen, each Y² and each Y³ are hydrogen, Y⁴ is hydrogen, and each of Y⁶, Y⁷ and Y⁸ is hydrogen, then each Y⁵ is deuterium.

In one embodiment each Y² is the same, each Y³ is the same and each Y⁵ is the same. In one aspect of this embodiment, each Y² is deuterium. In a further aspect each Y³ is deuterium. In another further aspect each Y³ is hydrogen. In another aspect of this embodiment, each Y² is hydrogen. In a further aspect each Y³ is deuterium. In another further aspect each Y³ is hydrogen. In one example of any of the foregoing aspects, Y¹ is deuterium. In another example of any of the foregoing aspects, Y¹ is hydrogen. In a more particular example of any of the foregoing aspects, Y¹ is deuterium, Y⁴ is deuterium, and each Y⁵ is deuterium. In another more particular example of any of the foregoing aspects, Y¹ is deuterium, Y⁴ is deuterium, and each Y⁵ is hydrogen. In another more particular example of any of the foregoing aspects, Y¹ is deuterium, Y⁴ is hydrogen, and each Y⁵ is hydrogen. In another more particular example of any of the foregoing aspects, Y¹ is hydrogen, Y⁴ is hydrogen, and each Y⁵ is hydrogen. In another more particular example of any of the foregoing aspects, Y¹ is hydrogen, Y⁴ is hydrogen, and each Y⁵ is deuterium. In another more particular example of any of the foregoing aspects, Y¹ is hydrogen, Y⁴ is deuterium, and each Y⁵ is deuterium. In another more particular example of any of the foregoing aspects, Y¹ is hydrogen, Y⁴ is deuterium, and each Y⁵ is hydrogen.

In one embodiment, Y⁶ is deuterium. In one aspect of this embodiment, each of Y⁷ and Y⁸ is deuterium. In another aspect of this embodiment, each of Y⁷ and Y⁸ is hydrogen.

In one embodiment, Y⁶ is hydrogen. In one aspect of this embodiment, each of Y⁷ and Y⁸ is deuterium. In another aspect of this embodiment, each of Y⁷ and Y⁸ is hydrogen.

In one embodiment, the compound is a compound of Formula I wherein Y⁶, Y⁷ and Y⁸ are each hydrogen and the compound is selected from any one of the compounds (Cmpd) set forth in Table 1 (below):

TABLE 1

Exemplary Embodiments of Formula I

| Cmpd | Y¹ | Each Y² | Each Y³ | Y⁴ | each Y⁵ |
|---|---|---|---|---|---|
| 100 | H | H | H | D | H |
| 101 | H | H | H | H | D |
| 102 | H | H | H | D | D |
| 103 | H | H | D | H | H |
| 104 | H | H | D | D | H |
| 105 | H | H | D | H | D |
| 106 | H | H | D | D | D |
| 107 | H | D | H | H | H |
| 108 | H | D | H | D | H |
| 109 | H | D | H | H | D |
| 110 | H | D | H | D | D |
| 111 | H | D | D | D | H |
| 112 | H | D | D | D | H |
| 113 | H | D | D | H | D |
| 114 | H | D | D | D | D |
| 115 | D | H | H | H | H |
| 116 | D | H | H | D | H |
| 117 | D | H | H | H | D |
| 118 | D | H | H | D | D |
| 119 | D | H | D | H | H |
| 120 | D | H | D | D | H |
| 121 | D | H | D | H | D |
| 122 | D | H | D | D | D |
| 123 | D | D | H | H | H |
| 124 | D | D | H | D | H |
| 125 | D | D | H | H | D |
| 126 | D | D | H | D | D |
| 127 | D | D | D | H | H |
| 128 | D | D | D | D | H |
| 129 | D | D | D | H | D |
| 130 | D | D | D | D | D | or a pharmaceutically acceptable salt thereof, wherein any atom not designated as deuterium is present at its natural isotopic abundance.

In one embodiment, the compound is a compound of Formula I wherein Y⁶, Y⁷ and Y⁸ are each D and the compound is selected from any one of the compounds (Cmpd) set forth in Table 2 (below):

TABLE 2

Exemplary Embodiments of Formula I

| Cmpd | Y¹ | Each Y² | Each Y³ | Y⁴ | each Y⁵ |
|---|---|---|---|---|---|
| 200 | H | H | H | D | H |
| 201 | H | H | H | H | D |
| 202 | H | H | H | D | D |
| 203 | H | H | D | H | H |
| 204 | H | H | D | D | H |
| 205 | H | H | D | H | D |
| 206 | H | H | D | D | D |
| 207 | H | D | H | H | H |
| 208 | H | D | H | D | H |
| 209 | H | D | H | H | D |
| 210 | H | D | H | D | D |
| 211 | H | D | D | H | H |
| 212 | H | D | D | D | H |
| 213 | H | D | D | H | D |
| 214 | H | D | D | D | D |
| 215 | D | H | H | H | H |
| 216 | D | H | H | D | H |

TABLE 2-continued

Exemplary Embodiments of Formula I

| Cmpd | Y¹ | Each Y² | Each Y³ | Y⁴ | each Y⁵ |
|------|----|---------|---------|----|---------|
| 217 | D | H | H | H | D |
| 218 | D | H | H | D | D |
| 219 | D | H | D | H | H |
| 220 | D | H | D | D | H |
| 221 | D | H | D | H | D |
| 222 | D | H | D | D | D |
| 223 | D | D | H | H | H |
| 224 | D | D | H | D | H |
| 225 | D | D | H | H | D |
| 226 | D | D | H | D | D |
| 227 | D | D | D | H | H |
| 228 | D | D | D | D | H |
| 229 | D | D | D | H | D |
| 230 | D | D | D | D | D |
| 231 | H | H | H | H | H | or a pharmaceutically acceptable salt thereof, wherein any atom not designated as deuterium is present at its natural isotopic abundance.

In another set of embodiments, any atom not designated as deuterium in any of the embodiments set forth above is present at its natural isotopic abundance.

The following compounds are useful for making various compounds of this invention:

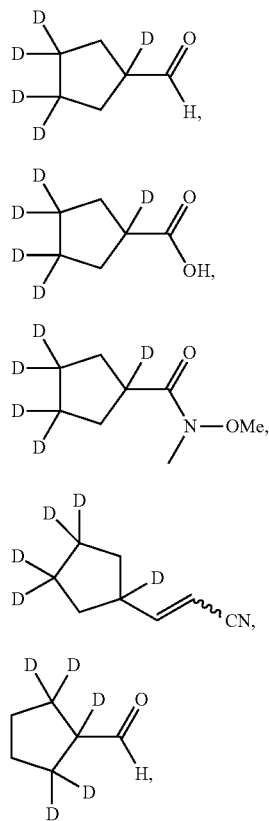

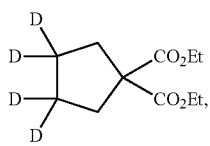

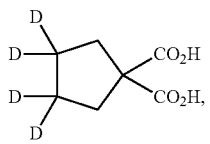

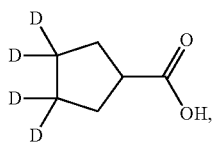

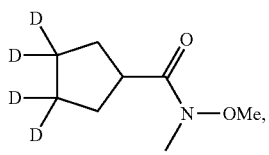

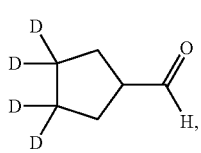

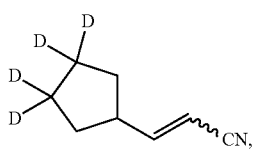

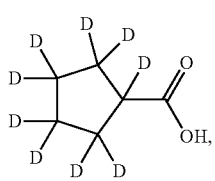

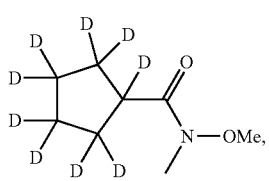

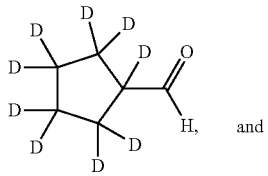

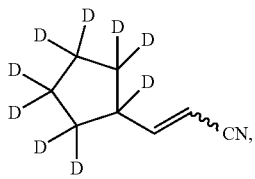

or a salt thereof, wherein any atom not designated as deuterium is present at its natural isotopic abundance.

The synthesis of compounds of Formula I or Formula A may be readily achieved by synthetic chemists of ordinary skill by reference to the Exemplary Synthesis and Examples disclosed herein. Relevant procedures analogous to those of use for the preparation of compounds of Formula I or Formula A and intermediates thereof are disclosed, for instance, in U.S. Pat. No. 7,598,257 and in Organic Letters, 2009, 11(9): 1999-2009.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Exemplary Synthesis

Compounds of Formula I or Formula A may be prepared in a manner analogous to those syntheses presented in U.S. Pat. No. 7,598,257 and in Organic Letters, 2009, 11(9): 1999-2009 using appropriately deuterated starting materials.

Compounds of Formula I or Formula A may also be prepared as shown in the schemes below.

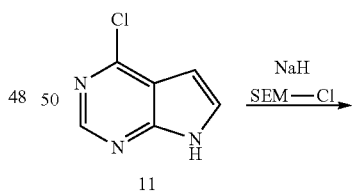

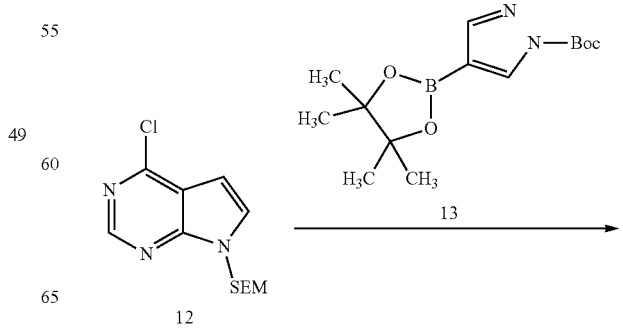

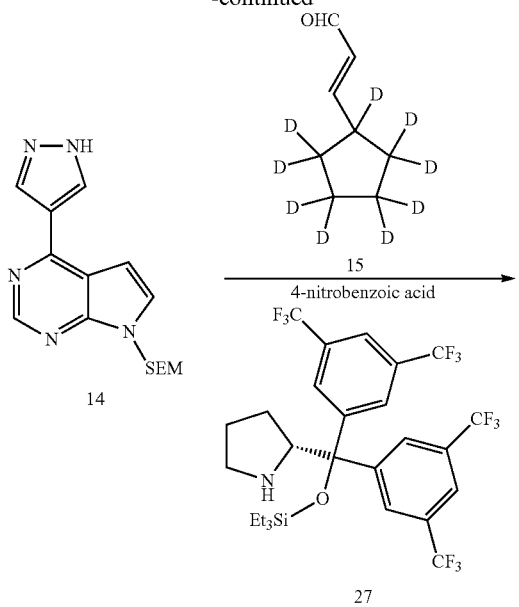

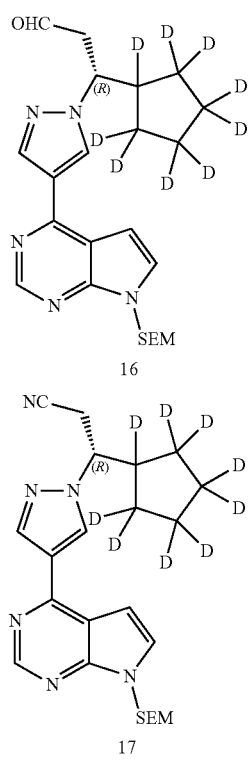

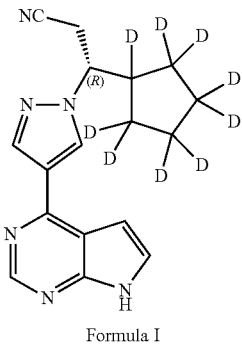

Scheme 1 discloses an exemplary preparation of the compound of formula I wherein $Y^1$, each $Y^2$ and each $Y^3$ are deuterium and $Y^4$, each $Y^5$, $Y^6$, $Y^7$ and $Y^8$ are hydrogen. In a manner analogous to that described in WO 2010/083283, commercially available, 4-chloro-7H-pyrrolo[2,3-d]pyrimidine 11 (Aldrich) is treated with sodium hydride and SEM chloride to afford 12, which is reacted with commercially available 13 to provide 14. Instead of 11, 4-bromo-7H-pyrrolo[2,3-d]pyrimidine may also be used in the first step to provide the SEM-protected 4-bromo-7H-pyrrolo[2,3-d]pyrimidine (analogous to 12) which can be reacted with 13 to provide 14. Reaction of 14 with 15, prepared as disclosed in Scheme 2a below, is performed in a manner analogous to that described in Lin, Q. et al. Org. Lett. 2009, 11, 1999, to give 16. The reaction is performed in the presence of chiral ligand 27, prepared as described in Lin, Q. et al. 16 is converted to 17 by treatment with $NH_4OH$ and $I_2$. The SEM protecting group of 17 is then deprotected with $LiBF_4$ and $NH_4OH$ to give a compound of Formula I.

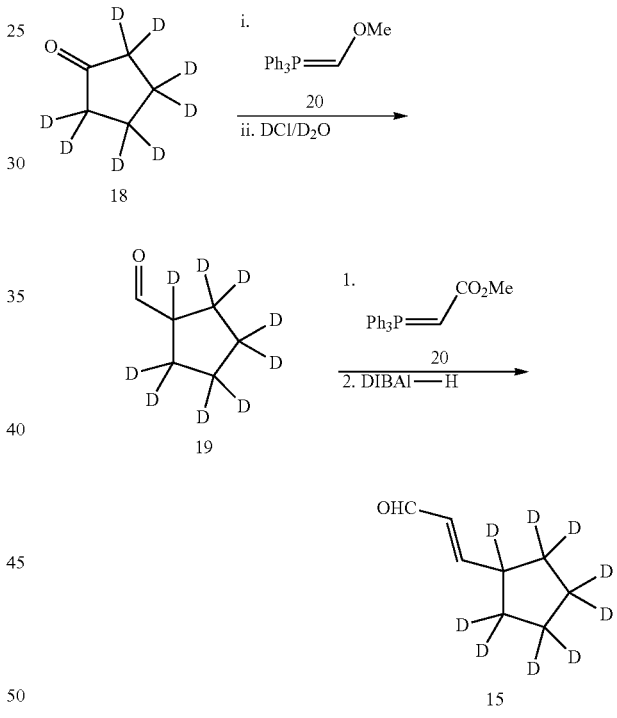

As shown in Scheme 2a, commercially available 18 is treated with phosphonium ylide 20 and $DCl/D_2O$ to provide 19, which is treated with 20 and DiBAl-H to afford 15.

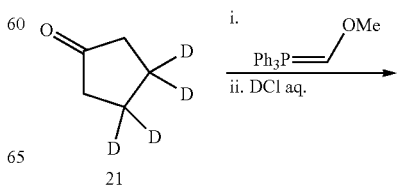

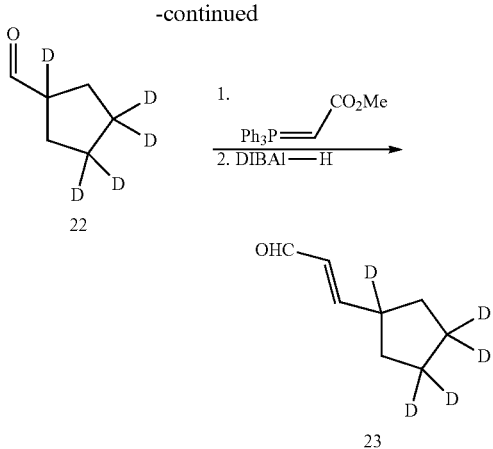

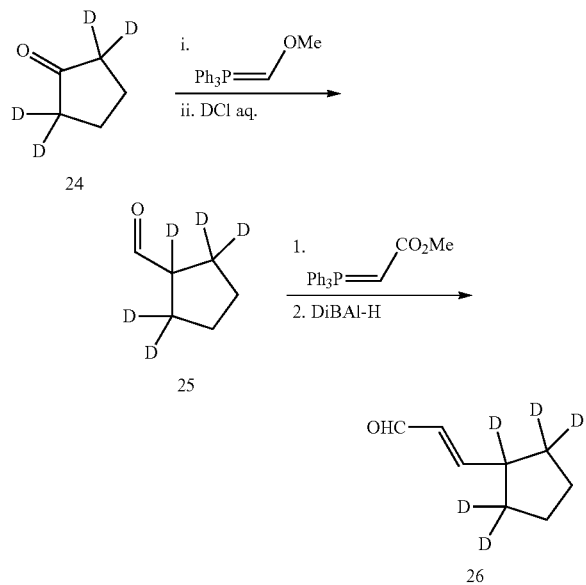

Compounds analogous to 15 may also be prepared. For example, as shown in Scheme 2b, commercially available 21 may be converted to 23 in a manner analogous to that disclosed in Scheme 2a. As another example, as shown in Scheme 2c, commercially available 24 may be converted to 26 in a manner analogous to that disclosed in Scheme 2a and Scheme 2b. 23 may be converted, in a manner similar to that disclosed in Scheme 1, to a compound of formula I wherein $Y^1$ and each $Y^3$ are deuterium and $Y^4$, each $Y^2$, each $Y^5$, $Y^6$, $Y^7$ and $Y^8$ are hydrogen. Likewise, 26 may be converted, in a manner similar to that disclosed in Scheme 1, to a compound of formula I wherein $Y^1$ and each $Y^2$ are deuterium and $Y^4$, each $Y^3$, each $Y^5$, $Y^6$, $Y^7$ and $Y^8$ are hydrogen.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art.

Additional methods of synthesizing compounds of Formula I or Formula A and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene, T W et al., *Protective Groups in Organic Synthesis*, 3$^{rd}$ Ed., John Wiley and Sons (1999); Fieser, L et al., *Fieser and Fieser's Reagents for Organic Synthesis*, John Wiley and Sons (1994); and Paquette, L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pyrogen-free pharmaceutical compositions comprising an effective amount of a compound of Formula I or Formula A (e.g., including any of the formulae herein), or a pharmaceutically acceptable salt of said compound; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the subject, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as ruxolitinib. Such agents include those indicated as being useful in combination with ruxolitinib.

Preferably, the second therapeutic agent is an agent useful in the treatment or prevention of a disease or condition selected from myelofibrosis, including primary myelofibrosis, polycythemia vera, post-polycythemia vera myelofibrosis, chronic idiopathic myelofibrosis, post-essential thrombocythemia myelofibrosis, and essential thrombocythemia, pancreatic cancer, prostate cancer, breast cancer, leukemia, non-Hodgkin's lymphoma, multiple myeloma, psoriasis and alopecia areata.

In one embodiment, the second therapeutic agent is selected from lenalidomide, panobinostat, capecitabine, exemestane, and combinations thereof.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat the target disorder.

The interrelationship of dosages for animals and humans (based on milligrams per meter squared of body surface) is described in Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y., 1970, 537.

In one embodiment, an effective amount of a compound of this invention can range from 1 mg to 500 mg, such as 5 mg to 100 mg, such as 5 mg to 50 mg. Examples of ranges are from 40 mg to 50 mg, from 25 mg to 40 mg, from 25 mg to 50 mg, from 20 mg to 40 mg, from 20 mg to 50 mg, from 10 mg to 25 mg, from 10 mg to 20 mg, from 5 mg to 25 mg, from 5 mg to 20 mg, and from 5 mg to 10 mg. In one embodiment, a dose of 10 mg, 20 mg, 40 mg, and 50 mg is administered once a day. In one embodiment a dose of 5 mg, 10 mg, 20 mg, 40 mg, and 50 mg is administered twice a day.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician. For example, guidance for selecting an effective dose can be determined by reference to the prescribing information for ruxolitinib.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of inhibiting one or more of Janus Associated Kinases (JAKs) JAK1 and JAK2 in a cell, comprising contacting a cell with one or more compounds of Formula I or Formula A herein, or a pharmaceutically acceptable salt thereof.

According to another embodiment, the invention provides a method of treating a disease that is beneficially treated by ruxolitinib in a subject in need thereof, comprising the step of administering to the subject an effective amount of a compound or a composition of this invention. In one embodiment the subject is a patient in need of such treatment. Such diseases are well known in the art and are disclosed in, but not limited to the following patent: U.S. Pat. No. 7,598,257. Such diseases include, but are not limited to, diseases involving the immune system including, for example, organ transplant rejection (e.g., allograft refection and graft versus host disease); autoimmune diseases such as multiple sclerosis, rheumatoid arthritis, juvenile arthritis, type I diabetes, lupus, psoriasis, inflammatory bowel disease, ulcerative colitis, Crohn's disease, myasthenia gravis, immunoglobulin nephropathies, autoimmune thyroid disorders; allergic conditions such as asthma, food allergies, atopic dermatitis and rhinitis; viral diseases such as Epstein Barr virus (EBV), hepatitis B, hepatitis C, HIV, HTLV 1, varicella-zoster virus (VZV) and human papilloma virus (HPV); skin disorders such as psoriasis (for example, psoriasis vulgaris), atopic dermatitis, skin rash, skin irritation, skin sensitization (e.g., contact dermatitis or allergic contact dermatitis; cancer, including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, melanoma), hematological cancers (e.g., lymphoma, leukemia such as acute lymphoblastic leukemia, or multiple myeloma), and skin cancer such as cutaneous T-cell lymphoma (CTCL) and cutaneous B-cell lymphoma (examples of which include Sezary syndrome and mycosis fungoides; myeloproliferative disorders (MPDs) such as polycythemia vera (PV), essential thrombocythemia (ET), myeloid metaplasia with myelofibrosis (MMM), chronic myelomonocytic leukemia (CMML), hypereosinophilic syndrome (HES), systemic mast cell disease (SMCD); inflammation and inflammatory diseases, such as inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis; systemic inflammatory response syndrome (SIRS) and septic shock; ischemia reperfusion injuries or a disease or condition related to an inflammatory ischemic event such as stroke or cardiac arrest; anorexia; cachexia; fatigue such as that resulting from or associated with cancer; restenosis; sclerodermitis; fibrosis; conditions associated with hypoxia or astrogliosis such as, for example diabetic retinopathy, cancer or neurodegeneration; gout; increased prostate size due to, e.g., benign prostatic hypertrophy or benign prostatic hyperplasia.

In one particular embodiment, the method of this invention is used to treat a disease or condition selected from myelofibrosis, including primary myelofibrosis, post-polycythemia vera myelofibrosis, post-essential thrombocythemia myelofibrosis, essential thrombocythemia or a combination thereof; pancreatic cancer; prostate cancer; breast cancer; leukemia, non-Hodgkin's lymphoma; multiple myeloma;psoriasis and a combination thereof in a subject in need thereof.

In another particular embodiment, the method of this invention is used to treat a disease or condition selected from myelofibrosis, including primary myelofibrosis, post-polycythemia vera myelofibrosis and post-essential thrombocythemia myelofibrosis in a subject in need thereof.

Identifying a subject in need of such treatment can be in the judgment of a subject or a health care professional and can be subjective (e.g. opinion) or objective (e.g. measurable by a test or diagnostic method).

In another embodiment, any of the above methods of treatment comprises the further step of co-administering to the subject in need thereof one or more second therapeutic agents. The choice of second therapeutic agent may be made from any second therapeutic agent known to be useful for co-administration with ruxolitinib. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In particular, the combination therapies of this invention include co-administering a compound of Formula I or Formula A and a second therapeutic agent to a subject in need thereof for treatment of the following conditions (with the particular second therapeutic agent indicated in parentheses following the indication: myelofibrosis (lenalidomide or panobinostat); pancreatic cancer (capecitabine); and breast cancer (exemestane).

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I or Formula A alone or together with one or more of the above-described second therapeutic agents in the manufacture of a medicament, either as a single composition or as separate dosage forms, for treatment or prevention in a subject of a disease, disorder or symptom set forth above. Another aspect of the invention is a compound of Formula I or Formula A for use in the treatment or prevention in a subject of a disease, disorder or symptom thereof delineated herein.

EXAMPLES

Example 1

Synthesis of (R)-3-(4-(7H-Pyrrolo[2,3-d]pyrimidin-4-yl)-1H-pyrazol-1-yl)-3-(2,2,5,5-$d_4$-cyclopentyl)propanenitrile (Compound 107)

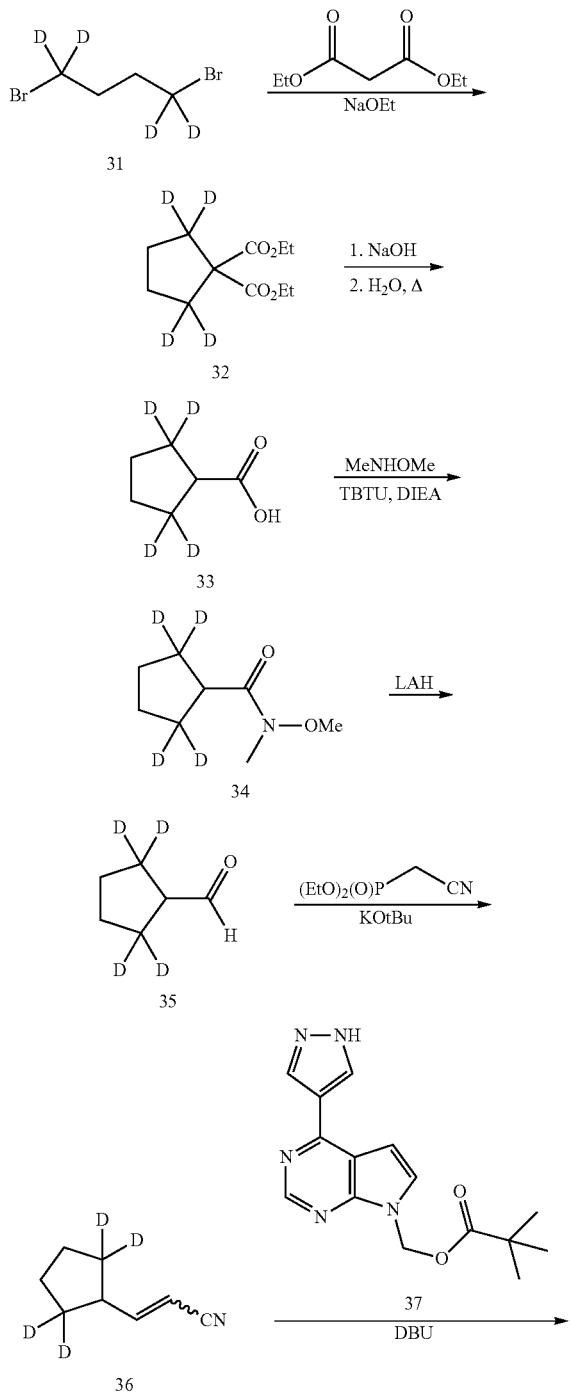

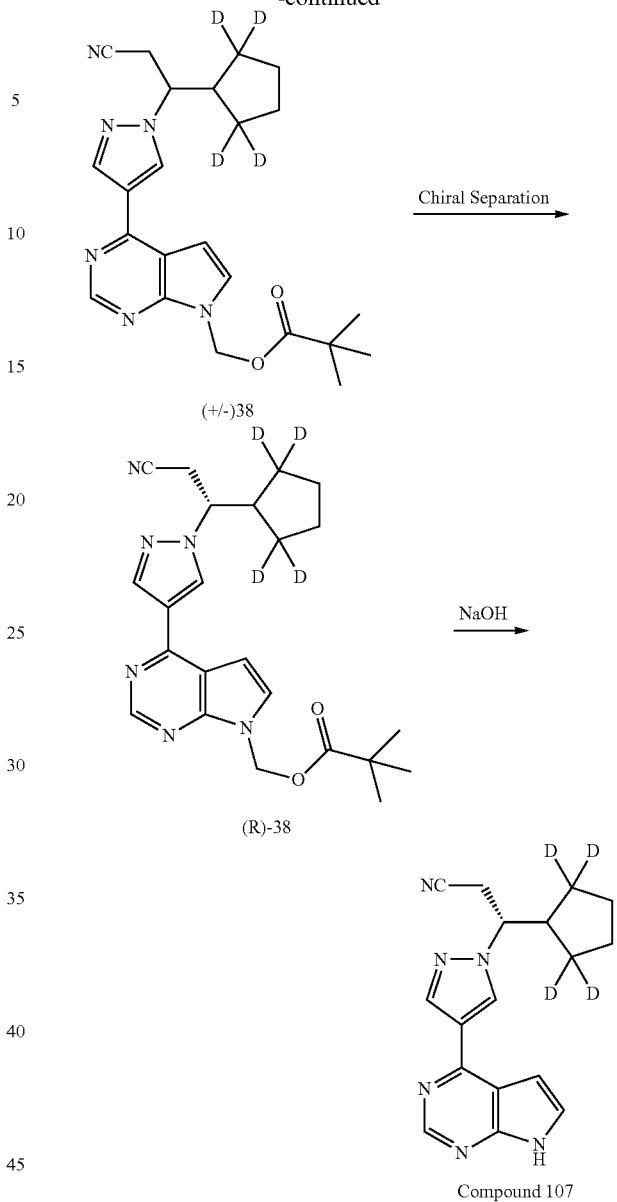

Step 1. Diethyl 2,2,5,5-$d_4$-cyclopentane-1,1-dicarboxylate (32). To a solution of diethyl malonate (6.57 mL, 43.3 mmol) in ethanol (40 mL) was added a 21 wt % solution of sodium ethoxide in ethanol (32.3 mL, 86.6 mmol) followed by 1,1,4,4-tetradeutero-1,4-dibromobutane (31, 5.53 mL, 45.5 mmol, CDN Isotopes, 98 atom % D). The resulting solution was stirred at reflux for two hours then cooled to room temperature and diluted with excess water. The majority of the ethanol was then removed via distillation and the resulting aqueous solution was extracted with ethyl acetate (3×75 mL). The organic layers were combined, washed with brine, dried (Na$_2$SO$_4$), filtered and concentrated under reduced pressure to afford 32 as a yellow oil which was carried forward without purification. (9.45 g, 100%).

Step 2. 2,2,5,5-$d_4$-Cyclopentane-1-carboxylic acid (33). To a solution of 32 (9.45 g, 43.3 mmol) in ethanol (20 mL) was added a 5M solution of sodium hydroxide (20 mL). Additional water (15 mL) was then added and the reaction stirred at reflux for three hours. Upon cooling to room temperature, the reaction was diluted with excess water and the majority of ethanol was removed via distillation. The aqueous solution was rendered acidic (pH<2) with 1N HCl and subsequently extracted with diethyl ether (3×50 mL). The organic layers were combined, dried ($Na_2SO_4$), filtered and concentrated under reduced pressure. The resulting light orange solid was transfered to a pressure flask and water (140 mL) was added. The pressure flask was sealed and the reaction stirred at 160° C. for 15 hours then was cooled to room temperature. The reaction was diluted with 1N HCl and extracted with diethyl ether (3×50 mL). The organic layers were combined, dried ($Na_2SO_4$), filtered and concentrated under reduced pressure to afford 33 (4.37 g, 86%) as an amber oil which was used without purification.

Step 3. 2,2,5,5-$d_4$-N-Methoxy-N-methylcyclopentanecarboxamide (34). To a solution of 33 (4.37 g, 37.0 mmol) in acetonitrile (60 mL) at 0° C. was added N,O-dimethylhydroxylamine hydrochloride (4.33 g, 44.4 mmol), TBTU (12.5 g, 38.9 mmol) and N,N-diisopropylethylamine (19.0 mL, 111 mmol). The reaction stirred at room temperature for 15 hours, then was diluted with 1N HCl and extracted with ethyl acetate (3×50 mL) The organic layers were combined, washed with sat. $NaHCO_3$, dried ($Na_2SO_4$), filtered and concentrated under reduced pressure. The reulting product was purified by column chromatography ($SiO_2$, 0-50% ethyl acetate/hexanes) to afford 34 (2.22 g, 37%) as a clear oil. MS (ESI) 162.3 [(M+H)$^+$].

Step 4. 2,2,5,5-$d_4$-Cyclopentane-1-carboxaldehyde (35). To a solution of 34 (2.22 g, 13.8 mmol) in THF (50 mL) at 0° C. was added dropwise a 1M solution of $LiAlH_4$ in THF (24.8 mL, 24.8 mmol). The reaction stirred at 0° C. for one hour then was quenched by sequential dropwise addition of water (940 μL), 15% NaOH (940 μL) and water (2.82 mL). The quenched reaction stirred at room temperature for 30 minutes then was filtered through Celite® and concentarted under reduced pressure. The resulting oil was diluted with 1N HCl and extracted with diethyl ether (3×50 mL). The organic layers were combined, dried ($Na_2SO_4$), filtered and concentrated under reduced pressure to afford 35 (850 mg, 60%) as a clear oil which was used without purification.

Step 5. 3-(2,2,5,5-$d_4$-cyclopentyl)acrylonitrile (36). To a 1M solution of potassium tert-butoxide in THF (8.74 mL, 8.74 mmol) at 0° C. was added dropwise a solution of diethyl cyanomethylphosphonate (1.48 mL, 9.15 mmol) in THF (12 mL). The reaction was warmed to room temperature, stirred for 15 minutes, then cooled to 0° C. Aldehyde 35 (850 mg, 8.32 mmol) was then added dropwise as a solution in THF (3 mL). The reaction was stirred at room temperature for 48 hours then diluted with excess water and extracted with diethyl ether (1×50 mL) and ethyl acetate (3×50 mL) The organic layers were combined, dried ($Na_2SO_4$), filtered and concentrated under reduced pressure to afford 36 (1.17 g, >100%) as a light orange oil which was used without purification.

Step 6. (+/−)-(4-(1-(2-Cyano-1-(2,2,5,5-$d_4$-cyclopentyl) ethyl)-1H-pyrazol-4-yl)-7H-pyrrolo[2,3-d]pyrimidin-7-yl) methyl pivalate ((+/−)38). To a solution of 37 (400 mg, 1.34 mmol, preparation described in Lin, Q. et al. *Org. Lett.*, 2009, 11, 1999-2002) in acetonitrile (10 mL) was added 36 (418 mg, 3.34 mmol) followed by DBU (421 μL, 2.81 mmol). The reaction stirred at room temperature for 15 hours then was concentrated under reduced vacuum. The resulting crude mixture was diluted with water and extracted with ethyl acetate (3×50 mL). The organic layers were combined, washed with 1N HCl, dried ($Na_2SO_4$), filtered and concentrated underreduced pressure. Purification via normal phase column chromatography ($SiO_2$, 0-60% ethyl acetate/hexanes) followed by reverse phase column chromatography (C18, 5-70% acetonitrile/water containing 0.1% formic acid) afforded (+/−)38 (68 mg, 12%) as a white foam. 1H NMR (DMSO-$d_6$, 400 MHz) δ 8.84 (s, 1H), 8.79 (s, 1H), 8.40 (s, 1H), 7.74 (d, J=3.8 Hz, 1H), 7.12 (d, J=3.8 Hz, 1H), 6.24 (s, 2H), 4.54 (td, J=9.7, 4.3 Hz, 1H), 3.30-3.15 (m, 2H), 2.39 (d, J=9.8 Hz, 1H), 1.68-1.36 (m, 4H), 1.08 (s, 9H); MS (ESI) 425.3 [(M+H)$^+$].

Step 7. (R)-(4-(1-(2-cyano-1-(2,2,5,5-tetradeuterocyclopentyl)ethyl)-1H-pyrazol-4-yl)-7H-pyrrolo[2,3-d]pyrimidin-7-yl)methyl pivalate ((R)-38). Racemic compound (+/−) 38 (62 mg) was dissolved in acetonitrile at a concentration of 30 mg/mL and subjected to chiral separation by preparative HPLC on a Daicel ChiralPak AD column (20×250 mm, 10 μm) with 500 μL of (+/−)38 solution per injection using an isocratic method: 30% isopropanol (+0.1% diethylamine)/ 70% hexane (+0.1% diethylamine) at a flow rate of 17 mL/min. Under these conditions baseline separation was achieved with (S)-38 eluting at 15.0 minutes and (R)-38 eluting at 20.2 minutes.

Fractions containing each enantiomer were pooled and concentrated yielding 28 mg of (S)-38 as a colorless film and 29 mg of (R)-38 as a colorless film.

Step 8. (R)-3-(4-(7H-Pyrrolo[2,3-d]pyrimidin-4-yl)-1H-pyrazol-1-yl)-3-(2,2,5,5-tetradeuterocyclopentyl)propanenitrile (Compound 107). Compound (R)-38 (28 mg, 0.066 mmol, 1 equiv) was dissolved in methanol (1 mL) in a 20 mL scintillation vial. Sodium hydroxide (0.13 mL of a 1 M solution, 0.13 mmol, 2 equiv) was added and the reaction was stirred at room temperature for 18 hours. The reaction was diluted with water (10 mL) and brine (20 mL). The aqueous mixture was extracted with ethyl acetate (2×20 mL). The combined organic layers were washed with brine (20 mL), dried over sodium sulfate, filtered, and evaporated. The crude material was purified using an Analogix automated chromatography system eluting with 0 to 6% methanol in dichloromethane. Product fractions were pooled and evaporated yielding compound 107 as a white foam. The chiral purity was found to be>99% ee (Chiralpak OD 4.6×250 mm, 10 um, 70% (hexane+0.1% diethylamine)+30% (isopropanol+0.1% diethylamine), 1 mL/min, 254 nm retention time=8.85 min).

Example 2

Synthesis of (R)-3-(4-(7H-Pyrrolo[2,3-d]pyrimidin-4-yl)-1H-pyrazol-1-yl)-3-(3,3,4,4-$d_4$-cyclopentyl) propanenitrile (Compound 103)

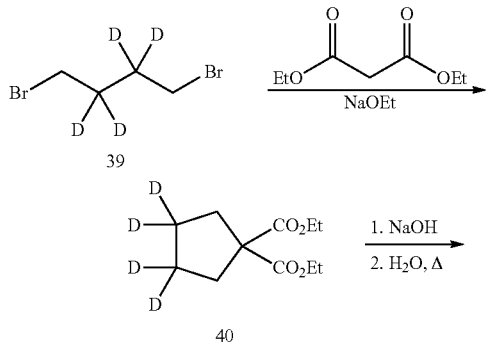

-continued

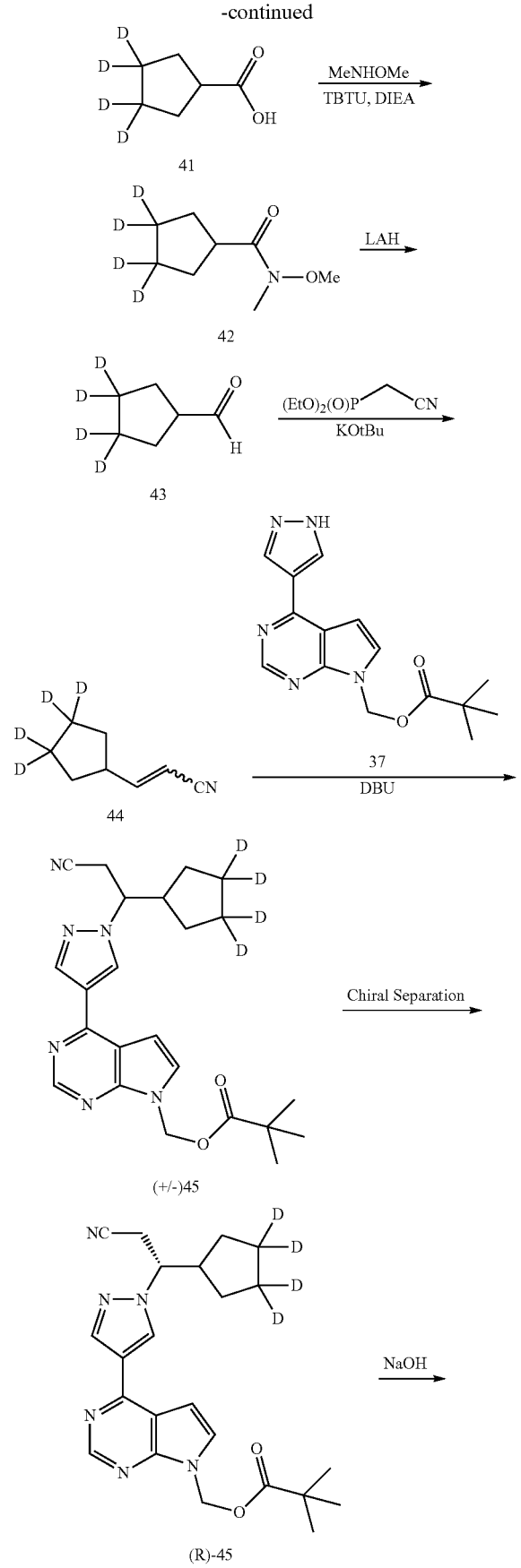

(+/-)45

(R)-45

-continued

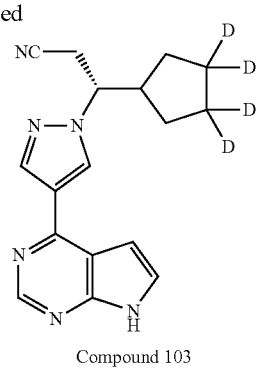

Compound 103

Step 1. Diethyl 3,3,4,4-$d_4$-cyclopentane-1,1-dicarboxylate (40). To a solution of diethyl malonate (3.25 mL, 21.4 mmol) in ethanol (20 mL) was added a 21 wt % solution of sodium ethoxide in ethanol (16.0 mL, 42.8 mmol) followed by 2,2,3,3-tetradeutero-1,4-dibromobutane (39, 4.95 g, 22.5 mmol, CDN Isotopes, 98 atom % D). The resulting solution was stirred at reflux for two hours then cooled to room temperature and diluted with excess water. The majority of the ethanol was then removed via distillation and the resulting aqueous solution was extracted with ethyl acetate (3×75 mL). The organic layers were combined, washed with brine, dried ($Na_2SO_4$), filtered and concentrated under reduced pressure to afford 40 as a yellow oil which was carried forward without purification. (4.67 g, 100%).

Step 2. 3,3,4,4-$d_4$-Cyclopentane-1-carboxylic acid (41). To a solution of 40 (4.67 g, 21.4 mmol) in ethanol (10 mL) was added a 5M solution of sodium hydroxide (10 mL). Additional water (10 mL) was then added and the reaction stirred at reflux for three hours. Upon cooling to room temperature, the reaction was diluted with excess water and the majority of ethanol was removed via distillation. The aqueous solution was rendered acidic (pH<2) with 1N HCl and subsequently extracted with diethyl ether (3×50 mL). The organic layers were combined, dried ($Na_2SO_4$), filtered and concentrated under reduced pressure. The resulting light orange solid was transfered to a pressure flask and water (70 mL) was added. The pressure flask was sealed and the reaction stirred at 160° C. for 15 hours then was cooled to room temperature. The reaction was diluted with 1N HCl and extracted with diethyl ether (3×50 mL). The organic layers were combined, dried ($Na_2SO_4$), filtered and concentrated under reduced pressure to afford 41 (1.93 g, 76%) as an amber oil which was used without purification.

Step 3. 3,3,4,4-$d_4$-N-Methoxy-N-methylcyclopentanecarboxamide (42). To a solution of 41 (1.93 g, 16.3 mmol) in acetonitrile (30 mL) at 0° C. was added N,O-dimethylhydroxylamine hydrochloride (1.91 g, 19.6 mmol), TBTU (5.50 g, 17.1 mmol) and N,N-diisopropylethylamine (8.52 mL, 48.9 mmol). The reaction stirred at room temperature for 15 hours, then was diluted with 1N HCl and extracted with ethyl acetate (3×50 mL). The organic layers were combined, washed with sat. $NaHCO_3$, dried ($Na_2SO_4$), filtered and concentrated under reduced pressure. The reulting product was purified by column chromatography ($SiO_2$, 0-40% acetone/hexanes) to afford 42 (1.47 g, 56%) as a clear oil. MS (ESI) 162.3 [(M+H)$^+$].

Step 4. 3,3,4,4-$d_4$-Cyclopentane-1-carboxaldehyde (43). To a soultion of 42 (1.47 g, 9.12 mmol) in THF (35 mL) at 0° C. was added dropwise a 1M solution of $LiAlH_4$ in THF (16.4 mL, 16.4 mmol). The reaction stirred at room temperature for one hour then was quenched at 0° C. by sequential dropwise addition of water (623 µL), 15% NaOH (623 µL) and water (1.87 mL). The quenched reaction stirred at room temperature for 30 minutes then was filtered through Celite® and concentarted under reduced pressure. The resulting oil was diluted with 1N HCl and extracted with diethyl ether (3×50 mL). The organic layers were combined, dried ($Na_2SO_4$), filtered and concentrated under reduced pressure to afford 43 (767 mg, 82%) as a clear oil which was used without purification.

Step 5. 3-(3,3,4,4-$d_4$-Cyclopentyl)acrylonitrile (44). To a solution of diethyl cyanomethylphosphonate (0.607 mL, 3.75 mmol) in THF (10 mL) at 0° C. was added dropwise a 1M solution of potassium tert-butoxide in THF (3.75 mL, 3.75 mmol). The reaction stirred at 0° C. for 1 hour. Aldehyde 43 (767 mg, 7.51 mmol) was then added dropwise as a solution in THF (3 mL). The reaction was stirred at room temperature for 15 hours then diluted with excess 1:1 water/brine and extracted with MTBE (3×50 mL). The organic layers were combined, dried ($Na_2SO_4$), filtered and concentrated under reduced pressure. The resulting oil was dissolved in $CH_2Cl_2$ (100 ml) and washed with $NaHSO_3$ (3×25 mL). The organic layer was dried ($Na_2SO_4$), filtered and concentrated under reduced pressure to afford 44 (537 mg, 57%) as a light orange oil which was used without purification.

Step 6. (+/−)-(4-(1-(2-Cyano-1-(3,3,4,4-$d_4$-cyclopentyl) ethyl)-1H-pyrazol-4-yl)-7H-pyrrolo[2,3-d]pyrimidin-7-yl) methyl pivalate ((+/−)45). To a solution of 37 (514 mg, 1.72 mmol, preparation described in Lin, Q. et al. *Org. Lett.*, 2009, 11, 1999-2002) in acetonitrile (15 mL) was added 44 (537 mg, 4.29 mmol) followed by DBU (540 µL, 3.61 mmol). The reaction stirred at room temperature for 15 hours then was concentrated under reduced vacuum. The resulting crude mixture was diluted with water and extracted with ethyl acetate (3×50 mL). The organic layers were combined, washed with 1N HCl, dried ($Na_2SO_4$), filtered and concentrated under reduced pressure. Purification via normal phase column chromatography ($SiO_2$, 0-60% ethyl acetate/hexanes) afforded (+/−) 45 (368 mg, 50%) as a white foam. 1H NMR (DMSO-$d_6$, 400 MHz) δ 8 8.84 (s, 1H), 8.79 (s, 1H), 8.40 (s, 1H), 7.75 (d, J=3.7 Hz, 1H), 7.12 (d, J=3.7 Hz, 1H), 6.24 (s, 2H), 4.53 (td, J=9.7, 4.2 Hz, 1H), 3.32-3.14 (m, 2H), 2.41 (q, J=8.7 Hz, 1H), 1.79 (dd, J=12.6, 7.6 Hz, 1H), 1.36-1.11 (m, 3H), 1.08 (s, 9H); MS (ESI) 425.2 [(M+H)$^+$].

Step 7. (R)-(4-(1-(2-Cyano-1-(3,3,4,4-$d_4$-cyclopentyp-ethyl)-1H-pyrazol-4-yl)-7H-pyrrolo[2,3-d]pyrimidin-7-yl) methyl pivalate ((R)-45). Racemic compound ((+/−)45 (151 mg) was dissolved in acetonitrile at a concentration of 30 mg/mL and subjected to chiral separation by preparative HPLC on a Daicel ChiralPak AD column (20×250 mm, 10 µm) with 1000 µL of (+/−)45 solution per injection using an isocratic method: 30% isopropanol (+0.1% diethylamine)/70% hexane (+0.1% diethylamine) at a flow rate of 17 mL/min. Under these conditions baseline separation was achieved with (S)-45 eluting at 15.5 minutes and (R)-45 eluting at 20.7 minutes.

Fractions containing each enantiomer were pooled separately and concentrated to give g 51 mg of (S)-45 as a colorless film and 53 mg of (R)-45 as a colorless film.

Step 8. (R)-3-(4-(7H-Pyrrolo [2,3-d]pyrimidin-4-yl)-1H-pyrazol-1-yl)-3-(3,3,4,4-$d_4$-cyclopentyl)propanenitrile (Compound 103). (R)-45 (53 mg, 0.13 mmol, 1 equiv) was dissolved in methanol (2 mL) in a 20 mL scintillation vial. Sodium hydroxide (0.25 mL of a 1 M solution, 0.25 mmol, 2 equiv) was added and the reaction mixture was stirred at room temperature for 18 hours. The reaction mixture was diluted with water (10 mL) and brine (20 mL). The aqueous mixture was extracted with ethyl acetate (2×20 mL). The combined organic layers were washed with brine (20 mL), dried over sodium sulfate, filtered, and concentrated. The crude material was purified using an Analogix automated chromatography system eluting with 0 to 6% methanol in dichloromethane. Product fractions were pooled and evaporated to give Compound 103 as a white foam in ~90% purity with the incompletely deprotected hydroxymethyl intermediate as the main impurity. Further chromatography failed to further improve the purity. The 90% pure material was dissolved in THF (2 mL) and treated with several drops of 10% aqueous sodium hydroxide at 40° C. for 8 hours resulting in complete conversion to Compound 103. The reaction mixture was diluted with water (10 mL) and extracted with ethyl acetate (2×10 mL). The combined organic layers were dried over sodium sulfate, filtered, and concentrated to a white foam. The foam was dissolved in minimal acetonitrile, diluted with water, and lyophilized to give Compound 103 (14 mg, 35% yield) as a white solid. The chiral purity was found to be>99% ee (Chiralpak OD 4.6×250 mm, 10 um, 70% (hexane+0.1% diethylamine)+30% (isopropanol+0.1% diethylamine), 1 mL/min, 254 nm retention time=7.56 min).

Example 3

Synthesis of (R)-3-(4-(7H-Pyrrolo[2,3-d]pyrimidin-4-yl)-1H-pyrazol-1-yl)-3-(cyclopentyl-$d_9$)propanenitrile (Compound 127)

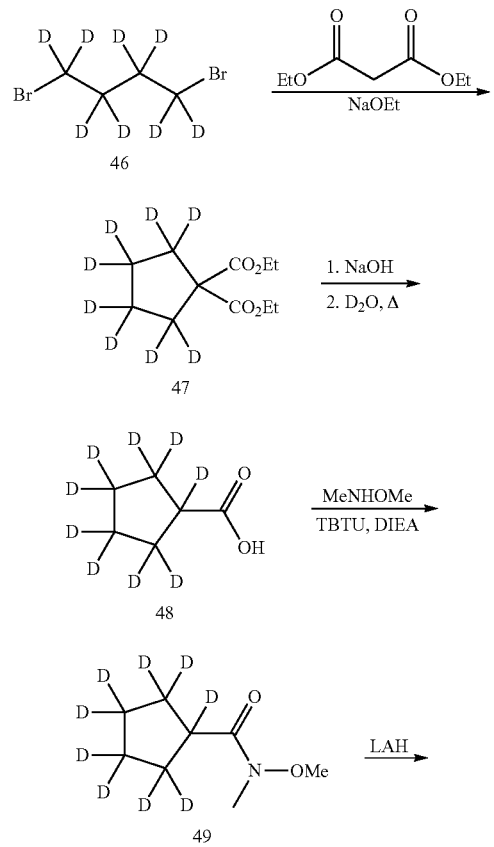

Scheme 5. Preparation of Compound 127

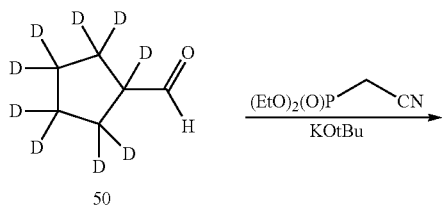

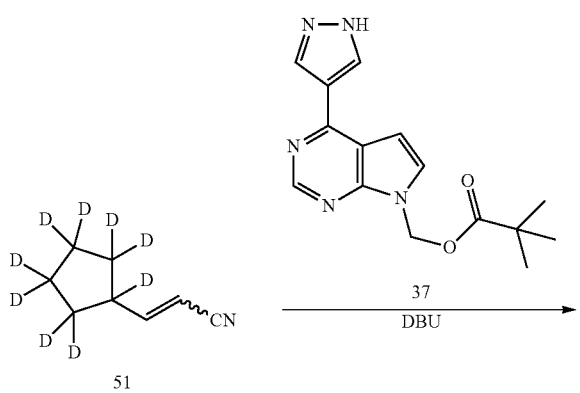

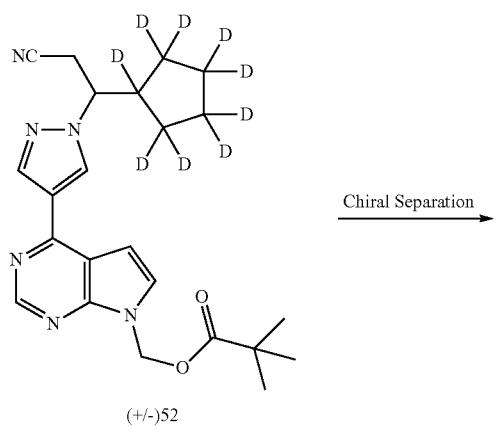

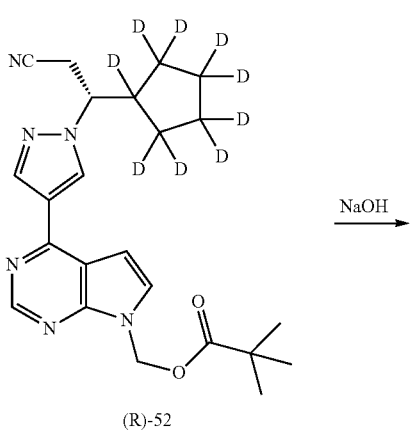

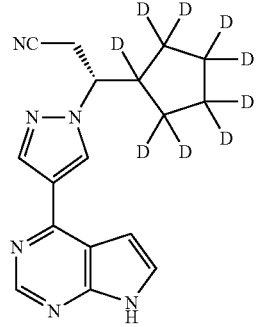

Compound 127

Step 1. Diethyl 2,2,3,3,4,4,5,5-$d_8$-Cyclopentane-1,1-dicarboxylate (47). To a solution of diethyl malonate (6.24 mL, 41.1 mmol) in ethanol (40 mL) was added a 21 wt % solution of sodium ethoxide in ethanol (30.7 mL, 82 2 mmol) followed by 1,1,2,2,3,3,4,4-octadeutero-1,4-dibromobutane (46, 9.67 g, 43.2 mmol, CDN Isotopes, 98 atom % D). The resulting solution was stirred at reflux for two hours then cooled to room temperature and diluted with excess water. The majority of the ethanol was then removed via distillation and the resulting aqueous solution was extracted with ethyl acetate (3×75 mL). The organic layers were combined, washed with brine, dried ($Na_2SO_4$), filtered and concentrated under reduced pressure to afford 47 as a yellow oil (9.12 g, 100%) which was carried forward without purification.

Step 2. Perdeuterocyclopentane-1-carboxylic acid (48). To a solution of 47 (9.12 g, 41.1 mmol) in ethanol (20 mL) was added a 5M solution of sodium hydroxide (20 mL). Additional water (15 mL) was then added and the reaction stirred at reflux for three hours. Upon cooling to room temperature, the reaction was diluted with excess water and the majority of ethanol was removed via distillation. The aqueous solution was rendered acidic (pH<2) with 1N HCl and subsequently extracted with diethyl ether (3×50 mL). The organic layers were combined, dried ($Na_2SO_4$), filtered and concentrated under reduced pressure. The resulting light orange solid was transfered to a pressure flask and $D_2O$ (120 mL) was added. The pressure flask was sealed and the reaction stirred at 160° C. for 15 hours then was cooled to room temperature. The reaction was diluted with 1N HCl and extracted with diethyl ether (3×50 mL). The organic layers were combined, dried ($Na_2SO_4$), filtered and concentrated under reduced pressure to afford 48 (4.58 g, 90%) as a yellow oil which was used without purification.

Step 3. N-Methoxy-N-methyl(cyclopentane-$d_9$)carboxamide (49). To a solution of 48 (4.58 g, 37.2 mmol) in acetonitrile (60 mL) at 0° C. was added N,O-dimethylhydroxylamine hydrochloride (4.35 g, 44.6 mmol), TBTU (12.5 g, 39 1 mmol) and N,N-diisopropylethylamine (19.4 mL, 112 mmol). The reaction stirred at room temperature for 15 hours, then was diluted with 1N HCl and extracted with ethyl acetate (3×50 mL). The organic layers were combined, washed with sat. $NaHCO_3$, dried ($Na_2SO_4$), filtered and concentrated under reduced pressure. The reulting product was purified by column chromatography ($SiO_2$, 0-50% ethyl acetate/hexanes) to afford 49 (3.41 g, 55%) as a clear oil. MS (ESI) 167.2 [(M+H)$^+$].

Step 4. Perdeuterocyclopentane-1-carboxaldehyde (50). To a solution of 49 (3.41 g, 20.5 mmol) in THF (80 mL) at 0° C. was added dropwise a 1M solution of $LiAlH_4$ in THF (37.0 mL, 37.0 mmol). The reaction stirred at room temperature for one hour then was quenched at 0° C. by sequential dropwise addition of D$_2$O (1.41 mL), 15% NaOD/D$_2$O (1.41 mL) and D$_2$O (4.23 mL). The quenched reaction stirred at room temperature for 30 minutes then was filtered through Celite® and concentrated under reduced pressure. The resulting oil was diluted with 1N DCl/D$_2$O and extracted with diethyl ether (3×50 mL). The organic layers were combined, dried (MgSO$_4$), filtered and concentrated under reduced pressure to afford 50 (1.79 g, 82%) as a clear oil which was used without purification.

Step 5. 3-(Perdeuterocyclopentyl)acrylonitrile (51). To a solution of diethyl cyanomethylphosphonate (1.35 mL, 8.34 mmol) in THF (25 mL) at 0° C. was added dropwise a 1M solution of potassium tert-butoxide in THF (8.34 mL, 8.34 mmol). The reaction stirred at 0° C. for 1 hour. Aldehyde 50 (1.79 g, 16.7 mmol) was then added dropwise as a solution in THF (5 mL). The reaction was stirred at room temperature for 15 hours then diluted with excess 1:1 water/brine and extracted with MTBE (3×50 mL) The organic layers were combined, dried (Na$_2$SO$_4$), filtered and concentrated underreduced pressure. The organic layers were combined, dried (Na$_2$SO$_4$), filtered and concentrated underreduced pressure to afford 51 (1.61 g, 74%) as a light orange oil which was used without purification.

Step 6. (+/−)-(4-(1-(2-Cyano-1-(cyclopentyl-d$_9$)ethyl)-1H-pyrazol-4-yl)-7H-pyrrolo[2,3-d]pyrimidin-7-yl)methyl pivalate ((+/−)52). To a solution of 37 (619 mg, 2.07 mmol, preparation described in Lin, Q. et al. *Org. Lett.*, 2009, 11, 1999-2002) in acetonitrile (15 mL) was added 51 (673 mg, 5.17 mmol) followed by DBU (650 µL, 4.35 mmol). The reaction stirred at room temperature for 15 hours then was concentrated under reduced vacuum. The resulting crude mixture was diluted with water and extracted with ethyl acetate (3×50 mL) The organic layers were combined, washed with 1N HCl, dried (Na$_2$SO$_4$), filtered and concentrated underreduced pressure. Purification via normal phase column chromatography (SiO$_2$, 0-60% ethyl acetate/hexanes) afforded (+/−)52 (447 mg, 50%) as a white foam. 1H NMR (DMSO-d$_6$, 400 MHz) δ 8.84 (s, 1H), 8.79 (s, 1H), 8.39 (s, 1H), 7.75 (d, J=3.7 Hz, 1H), 7.12 (d, J=3.7 Hz, 1H), 6.24 (s, 2H), 4.53 (dd, J=9.6, 4.2 Hz, 1H), 3.32-3.13 (m, 2H), 1.08 (s, 9H); MS (ESI) 430.3[(M+H)$^+$].

Step 7. (R)-(4-(1-(2-Cyano-1-(cyclopentyl-d$_9$)ethyl)-1H-pyrazol-4-yl)-7H-pyrrolo[2,3-d]pyrimidin-7-yl)methyl pivalate ((R)-52). Racemic compound (+/−)52 (162 mg) was dissolved in acetonitrile at a concentration of 30 mg/mL and subjected to chiral separation by preparative HPLC on a Daicel ChiralPak AD column (20×250 mm, 10 µm) with 1000 µL of (+/−)52 solution per injection using an isocratic method: 30% isopropanol (+0.1% diethylamine)/70% hexane (+0.1% diethylamine) at a flow rate of 17 mL/min. Under these conditions baseline separation was achieved with (S)-52 eluting at 15.4 minutes and (R)-52 eluting at 20.5 minutes.

Fractions containing each enantiomer were pooled separately and concentrated to give 61 mg of (S)-52 as a colorless film and 63 mg of (R)-52 as a colorless film.

Step 8. (R)-3-(4-(7H-Pyrrolo[2,3-d]pyrimidin-4-yl)-1H-pyrazol-1-yl)-3-(cyclopentyl-d$_9$)propanenitrile (Compound 127). (R)-52 (60 mg, 0.14 mmol, 1 equiv) was dissolved in methanol (2 mL) in a 20 mL scintillation vial. Sodium hydroxide (0.28 mL of a 1 M solution, 0.28 mmol, 2 equiv) was added and the reaction mixture was stirred at room temperature for 18 hours. The reaction mixture was diluted with water (10 mL) and brine (20 mL). The aqueous mixture was extracted with ethyl acetate (2×20 mL). The combined organic layers were washed with brine (20 mL), dried over sodium sulfate, filtered, and concentrated. The crude material was purified using an Analogix automated chromatography system eluting with 0 to 6% methanol in dichloromethane. Product fractions were pooled and evaporated to give Compound 127 (34 mg) as a white foam in ~90% purity with the incompletely deprotected hydroxymethyl intermediate as the main impurity. Further chromatography failed to further improve the purity. The 90% pure material was dissolved in THF (2 mL) and treated with several drops of 10% aqueous sodium hydroxide at 40° C. for 8 hours resulting in complete conversion to Compound 127. The reaction mixture was diluted with water (10 mL) and extracted with ethyl acetate (2×10 mL). The combined organic layers were dried over sodium sulfate, filtered, and concentrated to a white foam. The foam was dissolved in minimal acetonitrile, diluted with water, and lyophilized to give Compound 127 (19 mg, 42% yield) as a white solid. The chiral purity was found to be>99% ee (Chiralpak OD 4.6×250 mm, 10 um, 70% (hexane+0.1% diethylamine)+30% (isopropanol+0.1% diethylamine), 1 mL/min, 254 nm retention time=7.55 min).

Example 4

Evaluation of Metabolic Stability in CYP3A4 Supersomes™

Evaluation of Metabolic Stability of Compounds 103, 107 and 127 in Human CYP3A4 Supersomes™.

SUPERSOMES™ Assay. 10 mM stock solutions of test compounds, Compounds 103, 107, 127 and ruxolitinib, were prepared in DMSO. The 10 mM stock solutions were diluted to 15.6 µM in acetonitrile (ACN). Human CYP3A4 supersomes™ (1000 pmol/mL, purchased from BD Gentest™ Products and Services) were diluted to 62.5 pmol/mL in 0.1 M potassium phosphate buffer, pH 7.4, containing 3 mM MgCl$_2$. The diluted supersomes were added to wells of a 96-well polypropylene plate in triplicate. A 10 µL aliquot of the 15.6 µM test compound was added to the supersomes and the mixture was pre-warmed for 10 minutes. Reactions were initiated by addition of pre-warmed NADPH solution. The final reaction volume was 0.5 mL and contained 50 pmol/mL CYP3A4 supersomes™, 0.25 µM test compound, and 2 mM NADPH in 0.1 M potassium phosphate buffer, pH 7.4, and 3 mM MgCl$_2$. The reaction mixtures were incubated at 37° C., and 50 µL aliquots were removed at 0, 5, 10, 20, and 30 minutes and added to 96-well plates which contained 50 µL of ice-cold ACN with internal standard to stop the reactions. The plates were stored at 4° C. for 20 minutes after which 100 mL of water was added to the wells of the plate before centrifugation to pellet precipitated proteins. Supernatants were transferred to another 96-well plate and analyzed for amounts of parent remaining by LC-MS/MS using an Applied Biosystems API 4000 mass spectrometer.

Data analysis: The in vitro half-lives ($t_{1/2}$ values) for test compounds were calculated from the slopes of the linear regression of LN (% parent remaining) vs incubation time relationship:

$$\text{in vitro } t_{1/2} = 0.693/k$$

k=−[slope of linear regression of % parent remaining (ln) vs incubation time].

The results of this experiment are shown in Table 3 and FIG. 1. As shown in Table 3, the half-life of ruxolitinib was calculated to be 14.5 minutes. In contrast, each of Compounds 103, 107 and 127 were more stable in the supersomes with calculated half-lives of 16.9, 17.9 and 32.0 minutes respectively. This respresents a 17% increase in $t_{1/2}$ for compound 103, a 23% increase in $t_{1/2}$ for compound 107, and a 121% increase in $t_{1/2}$ for compound 127.

TABLE 3

Metabolic Stability of Compounds 103, 107 and 127 versus Ruxolitinib in Human CYP3A4 Supersomes ™

| | $t_{1/2}$ (minutes) | | |
|---|---|---|---|
| Compound | Experiment 1 | Experiment 2 | Ave ± SD |
| Ruxolitinib | 14.5 | 14.5 | 14.5 ± 00 |
| Compound 103 | 17.5 | 16.3 | 16.9 ± 0.9 (17%*) |
| Compound 107 | 18.4 | 17.0 | 17.9 ± 1.0 (23%*) |
| Compound 127 | 31.4 | 32.1 | 32.0 ± 0.5 (121%*) |

*% Δ = [(deuterated species) − (nondeuterated species)](100)/(nondeuterated species)

Example 5

Evaluation of Metabolic Stability in Human Liver Microsomes

Microsomal Assay: Human liver microsomes (20 mg/mL) are obtained from Xenotech, LLC (Lenexa, Kans.). β-nicotinamide adenine dinucleotide phosphate, reduced form (NADPH), magnesium chloride ($MgCl_2$), and dimethyl sulfoxide (DMSO) are purchased from Sigma-Aldrich.

Determination of Metabolic Stability: 7.5 mM stock solutions of test compounds are prepared in DMSO. The 7.5 mM stock solutions are diluted to 12.5-50 μM in acetonitrile (ACN). The 20 mg/mL human liver microsomes are diluted to 0.625 mg/mL in 0.1 M potassium phosphate buffer, pH 7.4, containing 3 mM $MgCl_2$. The diluted microsomes are added to wells of a 96-well deep-well polypropylene plate in triplicate. A 10 μL aliquot of the 12.5-50 μM test compound is added to the microsomes and the mixture is pre-warmed for 10 minutes. Reactions are initiated by addition of pre-warmed NADPH solution. The final reaction volume is 0.5 mL and contains 0.5 mg/mL human liver microsomes, 0.25-1.0 μM test compound, and 2 mM NADPH in 0.1 M potassium phosphate buffer, pH 7.4, and 3 mM $MgCl_2$. The reaction mixtures are incubated at 37° C., and 50 μL aliquots are removed at 0, 5, 10, 20, and 30 minutes and added to shallow-well 96-well plates which contain 50 μL of ice-cold ACN with internal standard to stop the reactions. The plates are stored at 4° C. for 20 minutes after which 100 μL of water is added to the wells of the plate before centrifugation to pellet precipitated proteins. Supernatants are transferred to another 96-well plate and analyzed for amounts of parent remaining by LC-MS/MS using an Applied Bio-systems API 4000 mass spectrometer. The same procedure is followed for the non-deuterated counterpart of the compound of Formula I or Formula A and the positive control, 7-ethoxycoumarin (1 μM). Testing is done in triplicate.

Data analysis: The in vitro $t_{1/2}$s for test compounds are calculated from the slopes of the linear regression of % parent remaining (ln) vs incubation time relationship.

in vitro $t_{1/2}$=0.693/k k=−[slope of linear regression of % parent remaining (ln) vs incubation time]

Data analysis is performed using Microsoft Excel Software.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

What is claimed is:

1. A compound of Formula A:

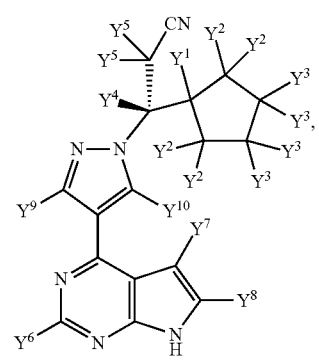

Formula A or a pharmaceutically acceptable salt thereof, wherein:

$Y^1$ is hydrogen;

each $Y^2$ is selected from hydrogen and deuterium, and each $Y^2$ is the same;

each $Y^3$ is selected from hydrogen and deuterium, and each $Y^3$ is the same;

$Y^4$ is selected from hydrogen and deuterium;

each $Y^5$ is the same and is selected from hydrogen and deuterium; and $Y^6$, $Y^7$, $Y^8$, $Y^9$ and $Y^{10}$ are each independently selected from hydrogen and deuterium; provided that:

each $Y^2$ is deuterium; or each $Y^3$ is deuterium; or each $Y^2$ and each $Y^3$ is deuterium.

2. The compound of claim 1, in which $Y^4$ is hydrogen and each $Y^5$ is hydrogen.

3. The compound of claim 1, in which each $Y^2$ is deuterium and each $Y^3$ is hydrogen.

4. The compound of claim 1, in which each $Y^2$ is hydrogen and each $Y^3$ is deuterium.

5. The compound of claim 1, in which each $Y^2$ is deuterium and each $Y^3$ is deuterium.

6. The compound of claim 1, in which $Y^6$, $Y^7$ and $Y^8$ are each hydrogen.

7. The compound of claim 1, in which the compound is selected from the group consisting of:

Compound 107

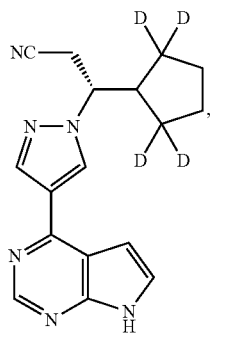

Compound 103

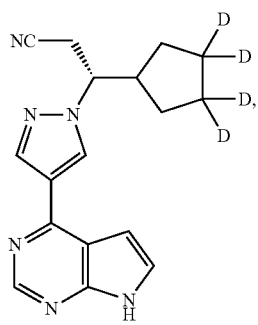
and

Compound 111

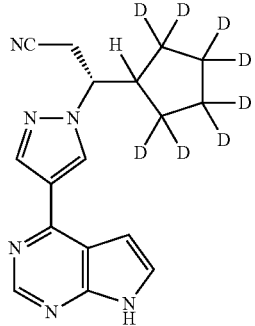

or a pharmaceutically acceptable salt of any of the foregoing.

8. A pharmaceutical composition comprising the compound of claim 1, and a pharmaceutically acceptable carrier.

9. A compound of Formula I:

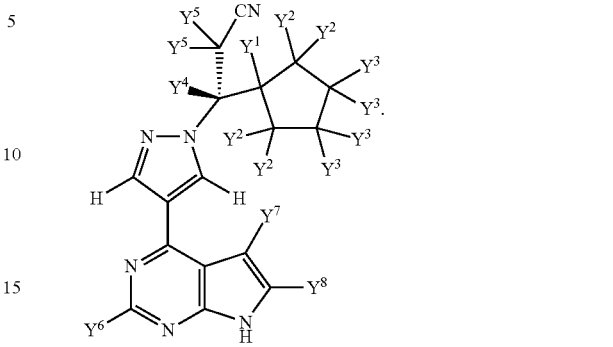

Formula I or a pharmaceutically acceptable salt thereof, wherein:
$Y^1$ is hydrogen;
each $Y^2$ is selected from hydrogen and deuterium, and each $Y^2$ is the same;
each $Y^3$ is selected from hydrogen and deuterium, and each $Y^3$ is the same;
$Y^4$ is selected from hydrogen and deuterium;
each $Y^5$ is the same and is selected from hydrogen and deuterium; and
$Y^6$, $Y^7$ and $Y^8$ are each independently selected from hydrogen and deuterium; provided that:
each $Y^2$ is deuterium; or
each $Y^3$ is deuterium; or
each $Y^2$ and each $Y^3$ is deuterium.

10. The compound of claim 9, in which $Y^4$ is hydrogen and each $Y^5$ is hydrogen.

11. The compound of claim 9, in which each $Y^2$ is deuterium and each $Y^3$ is hydrogen.

12. The compound of claim 9, in which each $Y^2$ is hydrogen and each $Y^3$ is deuterium.

13. The compound of claim 9, in which each $Y^2$ is deuterium and each $Y^3$ is deuterium.

14. The compound of claim 9, in which $Y^6$, $Y^7$ and $Y^8$ are each hydrogen.

15. A pharmaceutical composition comprising the compound of claim 9, and a pharmaceutically acceptable carrier.

* * * * *

(12) INTER PARTES REVIEW CERTIFICATE (3546th)

United States Patent
Silverman et al.

(10) Number: US 9,249,149 K1
(45) Certificate Issued: Apr. 2, 2024

(54) DEUTERATED DERIVATIVES OF RUXOLITINIB

(71) Applicants: I. Robert Silverman; Julie F. Liu; Adam J. Morgan; Bhaumik Pandya; Scott L. Harbeson

(72) Inventors: I. Robert Silverman; Julie F. Liu; Adam J. Morgan; Bhaumik Pandya; Scott L. Harbeson

(73) Assignee: SUN PHARMACEUTECALS INDUSTRIES, INC.

Trial Number:

IPR2017-01256 filed Apr. 7, 2017

Inter Partes Review Certificate for:

Patent No.: 9,249,149
Issued: Feb. 2, 2016
Appl. No.: 14/707,912
Filed: May 8, 2015

The results of IPR2017-01256 are reflected in this inter partes review certificate under 35 U.S.C. 318(b).

INTER PARTES REVIEW CERTIFICATE
U.S. Patent 9,249,149 K1
Trial No. IPR2017-01256
Certificate Issued Apr. 2, 2024

AS A RESULT OF THE INTER PARTES REVIEW PROCEEDING, IT HAS BEEN DETERMINED THAT:

Claims 1-15 are cancelled.

\* \* \* \* \*